(12) United States Patent
Sexton et al.

(10) Patent No.: US 12,178,633 B2
(45) Date of Patent: Dec. 31, 2024

(54) ATTACHMENT DEVICE FOR HOLDING AN AUSCULTATION DEVICE NEAR A SMART DEVICE

(71) Applicant: BioVentures, LLC, Little Rock, AR (US)

(72) Inventors: Kevin Wayne Sexton, Little Rock, AR (US); Joseph Allen Sanford, Jr., Little Rock, AR (US); Adria Abella Villafranca, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 121 days.

(21) Appl. No.: 17/797,538

(22) PCT Filed: Feb. 10, 2021

(86) PCT No.: PCT/US2021/017384
§ 371 (c)(1),
(2) Date: Aug. 4, 2022

(87) PCT Pub. No.: WO2021/163135
PCT Pub. Date: Aug. 19, 2021

(65) Prior Publication Data
US 2023/0050285 A1 Feb. 16, 2023

Related U.S. Application Data

(60) Provisional application No. 62/976,772, filed on Feb. 14, 2020.

(51) Int. Cl.
*H04R 1/46* (2006.01)
*A61B 5/00* (2006.01)
(Continued)

(52) U.S. Cl.
CPC ............... *A61B 7/04* (2013.01); *H04R 1/46* (2013.01); *H04R 3/00* (2013.01); *A61B 5/6898* (2013.01)

(58) Field of Classification Search
CPC ........... H04R 1/46; A61B 7/04; A61B 5/6898; G10K 11/22
See application file for complete search history.

(56) References Cited

U.S. PATENT DOCUMENTS 8,286,789 B2 10/2012 Wilson
9,042,568 B2 5/2015 Poplaw
(Continued)

FOREIGN PATENT DOCUMENTS

JP 6022739 11/2016
JP 6582261 * 9/2019

OTHER PUBLICATIONS

Machine translation of JP 6582261, 17 pages. (Year: 2019).*
(Continued)

*Primary Examiner* — Ping Lee
(74) *Attorney, Agent, or Firm* — Richard Blakely Glasgow

(57) ABSTRACT

An attachment device for holding an auscultation device near a smart device. The attachment device includes an interior compartment for receiving the smart device and a port for receiving the auscultation device. In use, the attachment device holds the microphone of the smart device adjacent to the auscultation device. The smart device records the heart or breathing sounds from the auscultation device, and a mobile application on the smart device classifies the sounds as normal or abnormal.

7 Claims, 10 Drawing Sheets

(51) Int. Cl.
    *A61B 7/04*           (2006.01)
    *H04R 3/00*         (2006.01)

(56) References Cited

U.S. PATENT DOCUMENTS

| | | |
|---|---|---|
| 2009/0294617 A1 | 12/2009 | Stacey |
| 2012/0190303 A1 | 7/2012 | Wong |
| 2014/0163422 A1 | 6/2014 | Poplaw |
| 2015/0104027 A1 | 4/2015 | Mulumudi |
| 2016/0192846 A1 | 7/2016 | Shekhar |

OTHER PUBLICATIONS

Machine translation of JP 6582261, 29 pages. (Year: 2019).*
International Search Report and Written Opinion, International Application No. PCT/US21/17384 (Jul. 22, 2021).

\* cited by examiner

ATTACHMENT DEVICE FOR HOLDING AN AUSCULTATION DEVICE NEAR A SMART DEVICE

CROSS-REFERENCE TO RELATED APPLICATIONS

This application claims the benefit of U.S. Provisional Application No. 62/976,772, entitled "Attachment Device for Holding an Auscultation Device Near a Smart Device" and filed on Feb. 14, 2020. The complete disclosure of said provisional application is hereby incorporated by reference.

STATEMENT REGARDING FEDERALLY SPONSORED RESEARCH OR DEVELOPMENT

Not applicable

BACKGROUND ART

A stethoscope is a medical device for auscultation or listening to the internal sounds of a human. A stethoscope commonly includes a small disc-shaped resonator that is placed against the skin (also called a chest piece) and a pair of tubes connected to earpieces. A stethoscope can be used to listen to the sounds made by the heart, lungs, and intestines. A stethoscope may also be used to listen to the sounds made by blood flow in arteries and veins. A major drawback of the prior art stethoscope is that it cannot be used in the remote diagnosis and treatment of patients, which is commonly referred to as telemedicine or telehealth. Telemedicine is particularly important in rural areas because of lack of local medical care. There are electronic stethoscopes that electronically connect to smartphones through the audio jack or the charging port, but they contain electrical components that make them complex and expensive.

It would therefore be desirable to develop an attachment device for holding an auscultation device near a smart device for recording and analyzing heart and breathing sounds without the necessity of extra electronics.

DISCLOSURE OF THE INVENTION

The present invention is directed to an attachment device for holding an auscultation device near a smart device. The attachment device includes an interior compartment for receiving the smart device and a port for receiving the auscultation device. In use, the attachment device holds the microphone of the smart device adjacent to the auscultation device. The smart device records the heart and breathing sounds using the auscultation device, and a mobile application on the smart device utilizing an artificial intelligence algorithm classifies the sounds as normal or abnormal.

These and other features, objects and advantages of the present invention will become better understood from a consideration of the following detailed description of the preferred embodiments and appended claims in conjunction with the drawings as described following:

DETAILED DESCRIPTION OF THE INVENTION

Figure 1:
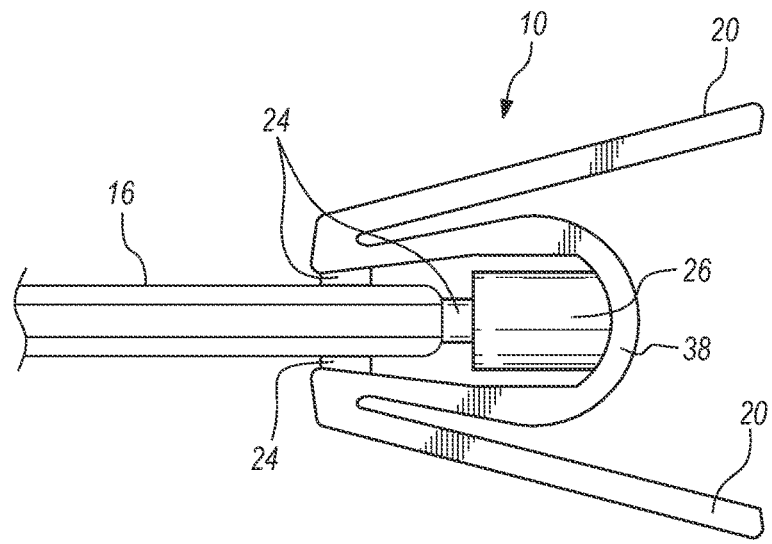
FIG. 1 is a side perspective view of a first preferred embodiment of the attachment device holding a smartphone.

With reference to FIGS. 1-14D, the preferred embodiments of the present invention may be described. The attachment device 10 of the present invention is a mechanical device for holding an auscultation device 12 in close proximity (or adjacent) to the microphone 14 of a smart device 16 (such as a smartphone) for recording heart and breathing sounds to permit later analysis by a medical professional. Thus, the attachment device 10 is configured to hold a smart device 16 and to receive an auscultation device 12. While the auscultation device 12 is preferably a stethoscope chest piece 18 comprising a bell 36 or diaphragm, the attachment device 10 is configured to receive a wide variety of auscultation devices.

The attachment device 10 is also configured to hold a variety of different sized smartphones and other electronic devices capable of recording sound. For example, the smart device 16 may be an iPhone® smartphone or an iPad® device. The attachment device 10 is preferably made of Polylactic Acid (PLA) because it is relatively inexpensive and easy for 3D printing. However, the attachment device 10 may alternatively be made of other hard and durable materials. In addition to being durable so the device may be reused, it is preferable that the attachment device 10 be made of materials that allow the device to be easily cleaned.

As shown in FIG. 1, the attachment device 10 is a clip in the first embodiment with two arms 20 joined on opposite sides of a connection portion 38. Thus, the attachment device 10 includes two arms 20 that when pressed towards one another allows access to the interior 22 of the connection portion 38 of the attachment device 10. The interior 22 may alternatively be referred to as an interior compartment 22.

The interior 22 is configured to receive an end of the smart device 16. The interior 22 of the attachment device 10 preferably is shallow enough that none of the screen of the smart device 16 is obstructed by the attachment device 10. Rubber or elastic cushions 24 are attached in the interior 22 of the attachment device 10. When the smart device 16 is positioned in the interior 22 of the attachment device 10, the smart device 16 preferably is only contacted by the cushions 24. The cushions are made of material with a high coefficient of friction in order to provide secure points of fixation for the smart device 16 and the attachment device 10. In addition, the cushions provide sound insulation. As shown in FIG. 1, in one embodiment, there are three cushions. The cushions are preferably positioned on opposite sides of the opening to the interior 22 and at the bottom of the interior 22 of the attachment device 10.

Figure 2:
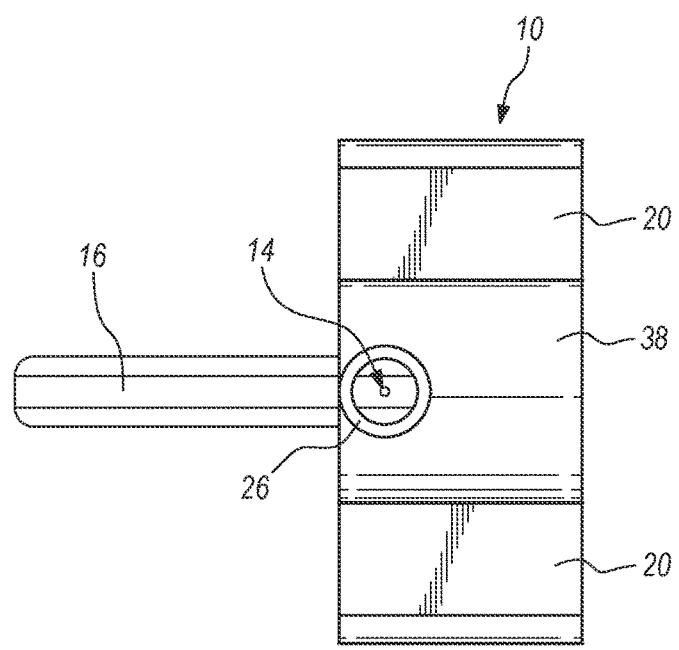
FIG. 2 is a back view of a first preferred embodiment of the attachment device holding a smartphone.
Figure 3:
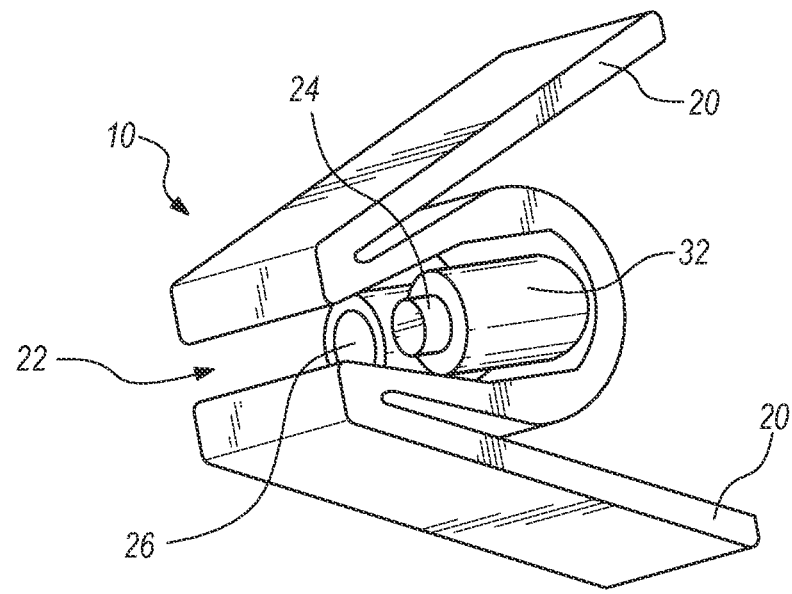
FIG. 3 is a side perspective view of a first preferred embodiment of the attachment device.
Figure 4:
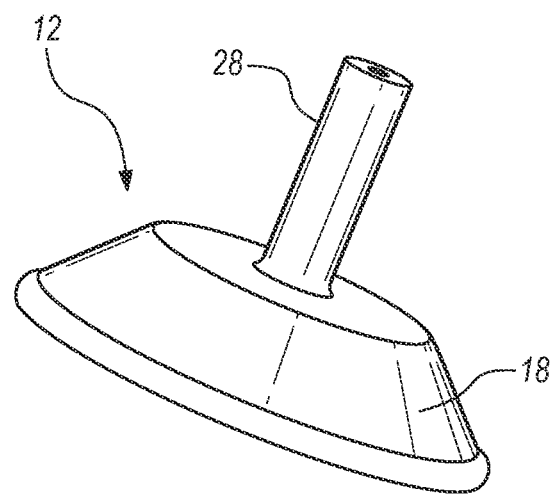
FIG. 4 is a side perspective view of the stethoscope chest piece of the present invention.

As shown in FIG. 2, the attachment device 10 includes a port 26 preferably positioned in the bottom of the interior 22. When the smart device 16 is positioned in the attachment device 10, the microphone 14 at the base of the smart device 16 is preferably positioned adjacent to the port 26. The port 26 is preferably cylindrical and extends into the interior 22 of the attachment device 10, as shown in FIGS. 2-3. The bottom of the interior 22 also includes a support 32 on which the smart device 16 rests. This allows the smart device 16 to sit straight with the microphone properly aligned with the port. The support 32 is cylindrical in one embodiment but it may alternatively be different shapes. The support 32 also provides stability to the attachment device when the smart device is attached to the attachment device. A cushion 24 is preferably attached to the top of the support 32, as shown in FIGS. 1 and 3.

Figure 5:
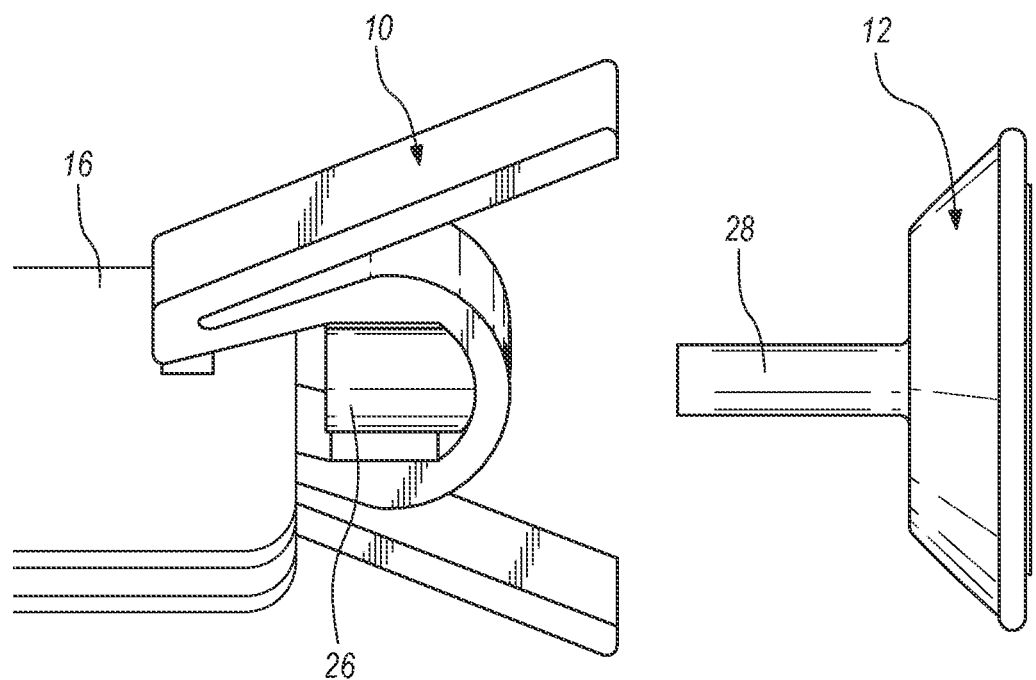
FIG. 5 is a top perspective view of a first preferred embodiment of the attachment device holding a smartphone before insertion of the stethoscope chest piece.
Figure 6:
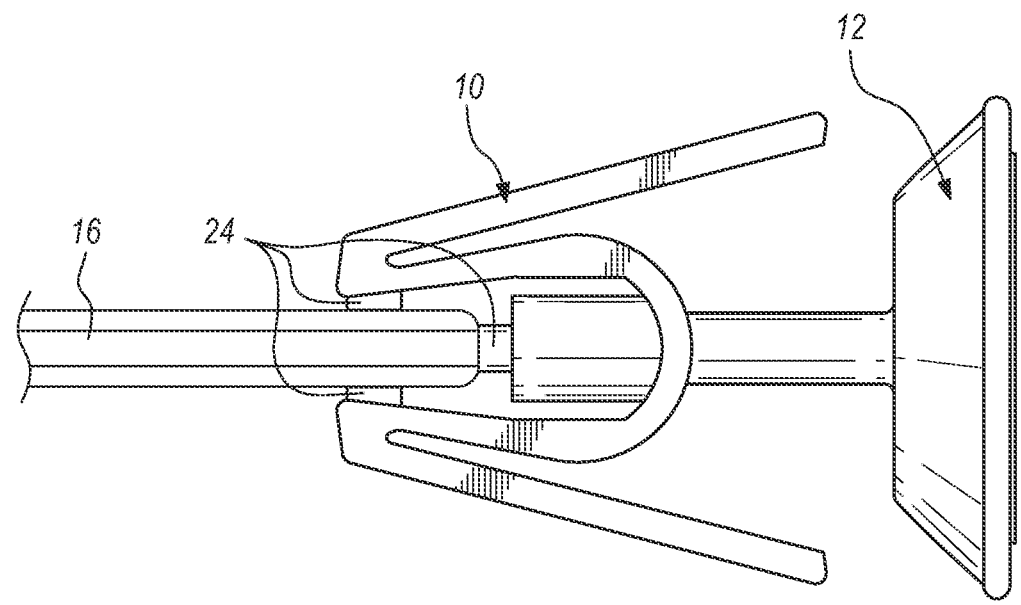
FIG. 6 is a side perspective view of a first preferred embodiment of the attachment device holding a smartphone as the stethoscope chest piece is being inserted into the attachment device.
Figure 7:
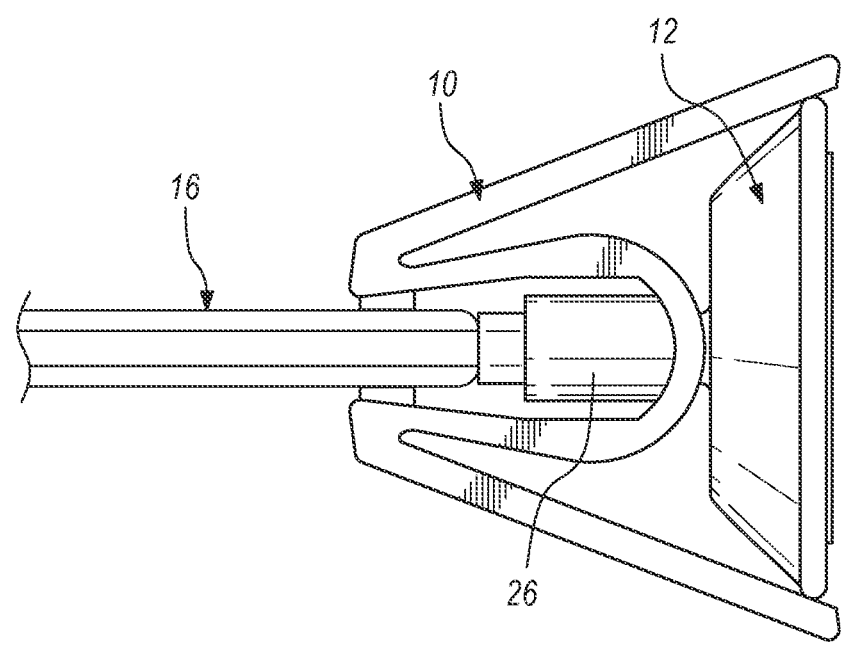
FIG. 7 is a side perspective view of a first preferred embodiment of the attachment device holding a smartphone and attached to the stethoscope chest piece.
Figure 8:
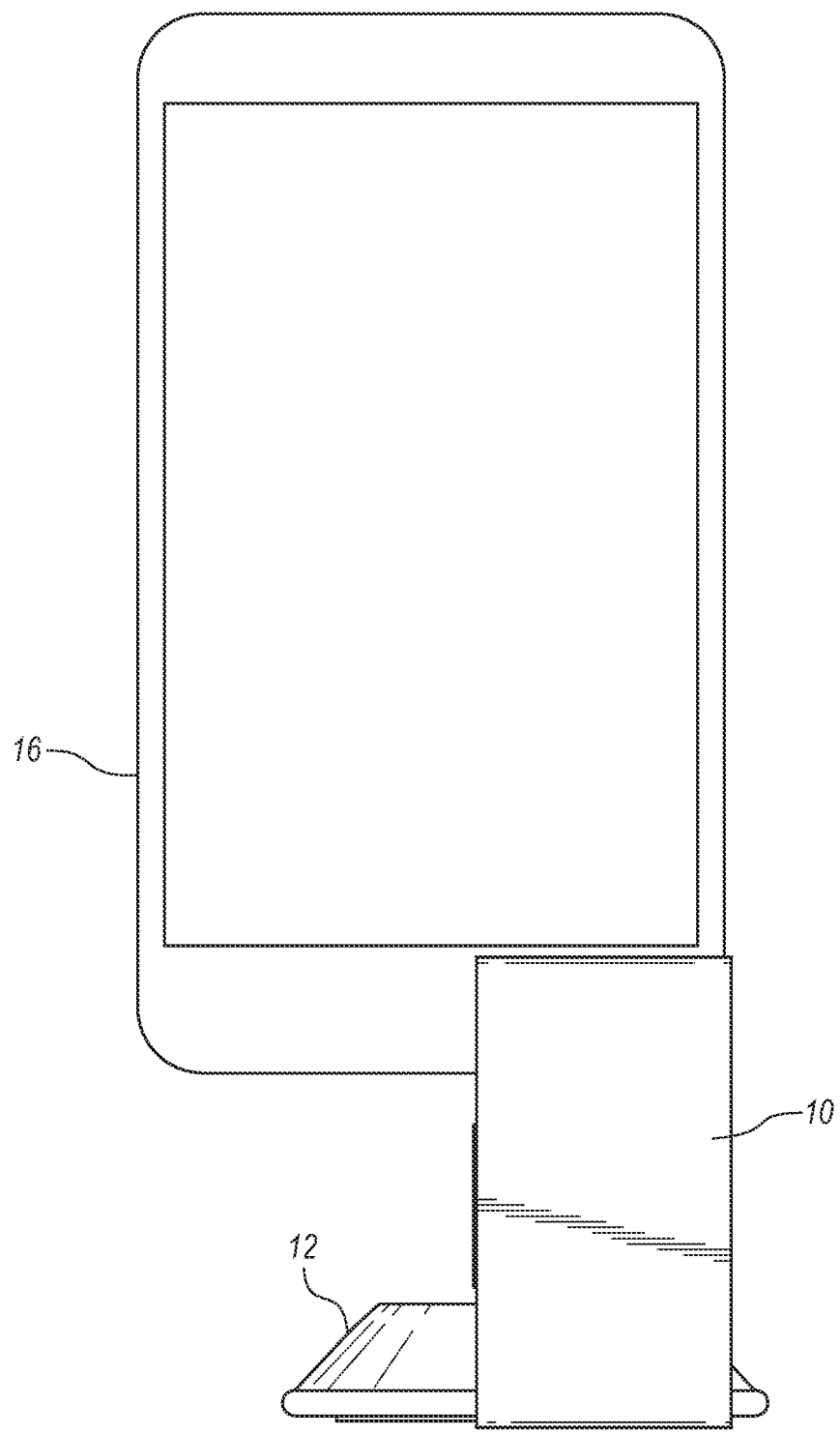
FIG. 8 is a top perspective view of a first preferred embodiment of the attachment device holding a smartphone and attached to the stethoscope chest piece.

After the smart device 16 is positioned in the interior 22 of the attachment device 10, the auscultation device 12 is connected to the port 26 of the attachment device. In one embodiment, a portion of the auscultation device 12 is received in the port 26, as shown in FIGS. 5-7. For example, in one embodiment, the neck 28 of the stethoscope chest piece 18 is received in the port 26. The neck 28 is pushed into the port 26 until the end of the neck is touching the surroundings of the microphone 14 of the smart device 16.

In one embodiment, as shown in FIGS. 4-5 and 14A-D, the neck 28 of the stethoscope chest piece 18 extends perpendicularly to the face of the bell 36. This configuration of the stethoscope chest piece 18 permits easy attachment to the attachment device 10. In this embodiment, the neck 28 of the stethoscope chest piece 18 is larger than the neck of the prior art stethoscope chest piece 18 that extends parallel to the face of the bell 36. The stethoscope chest piece 18 has acoustic space or channeling that maximizes certain frequencies for specific sounds. In this regard, the stethoscope chest piece 18 is configured to filter noise and bad signals for easier analysis and more accurate diagnosis.

Figure 9:
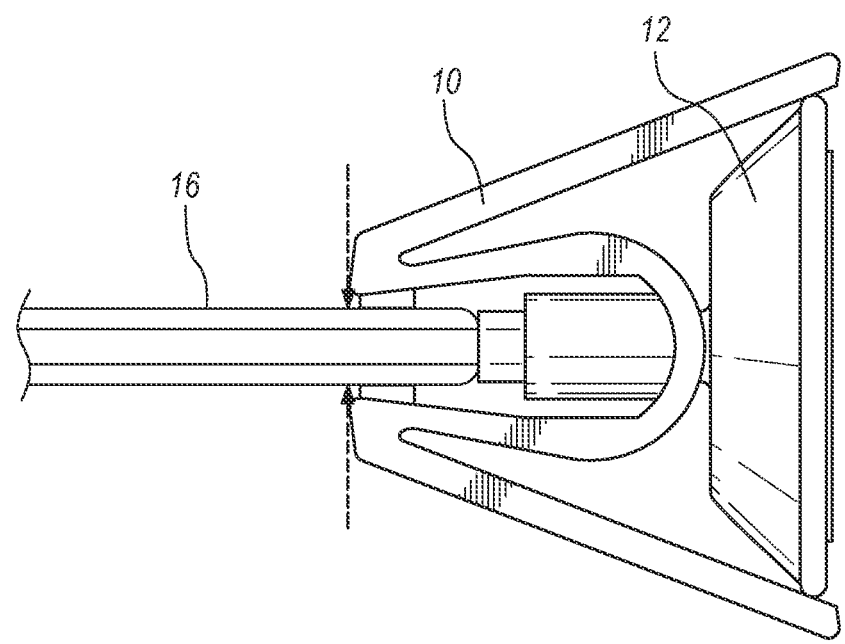
FIG. 9 is a side perspective view of a first preferred embodiment of the attachment device holding a smartphone and attached to the stethoscope chest piece.

When the auscultation device 12 is attached to the attachment device 10, the auscultation device 12 prevents the arms 20 of the attachment device 10 from being bent. This is achieved because the arms 20 contact the auscultation device 12, as shown in FIG. 9. Since the arms 20 cannot be bent, a force (as shown by the arrows in FIG. 9) is applied on the smart device 16 from the walls of the interior 22 of the attachment device. As a result, both the auscultation device 12 and the smart device 16 are firmly secured to the attachment device.

Once the smart device 16 and the auscultation device 12 are attached to the attachment device 10, the patient, patient's caregiver or a medical professional opens a mobile app on the smart device 16 for recording and processing the sounds received from the auscultation device 12. In one embodiment, the smart device 16 (through the app) records the sound, filters it through an artificial intelligence algorithm, plots an image of the sound and sends it to the medical professional. The artificial intelligence algorithm filters background noise using low pass and high pass filters which makes the sound of interest clearer and louder. Depending on the particular issue with the patient, the app may be set for a heartbeat analysis, heart rhythm analysis, breathing sounds analysis, carotid bruit sound analysis, or another analysis. The medical professional receives the image of the sound with a recording of the sound through the app on his or her smart device which permits the medical professional to make a diagnosis.

Figure 13:
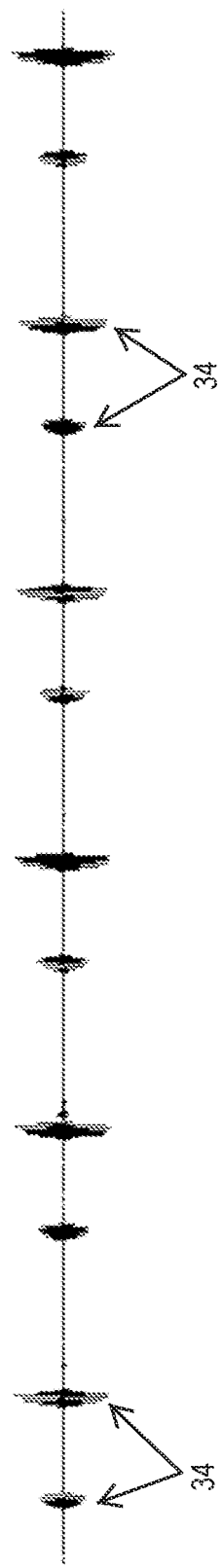
FIG. 13 is an illustration of the sound waves from testing of the first preferred embodiment of the attachment device.
Figure 14A:
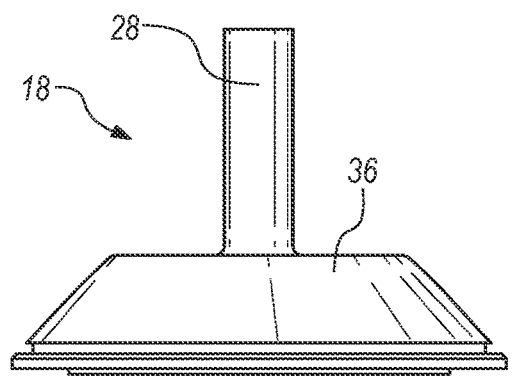
FIG. 14A is a side view of the stethoscope chest piece of the present invention.
Figure 14B:
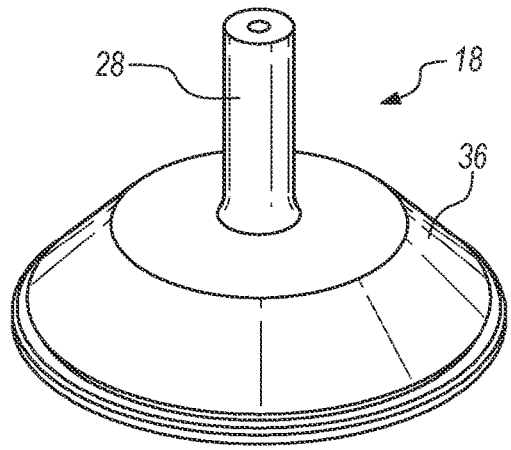
FIG. 14B is a top perspective view of the stethoscope chest piece of the present invention.
Figure 14C:
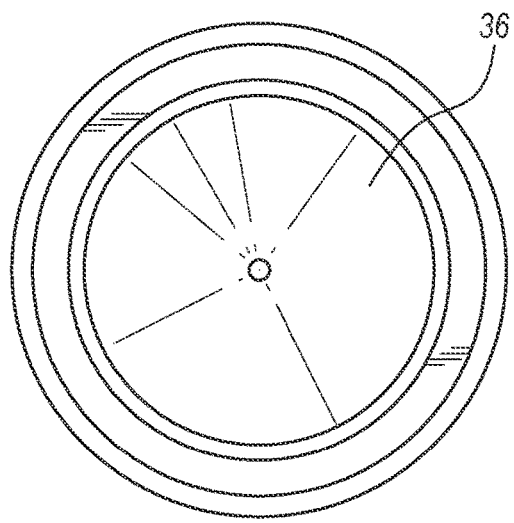
FIG. 14C is a bottom view of the stethoscope chest piece of the present invention.
Figure 14D:
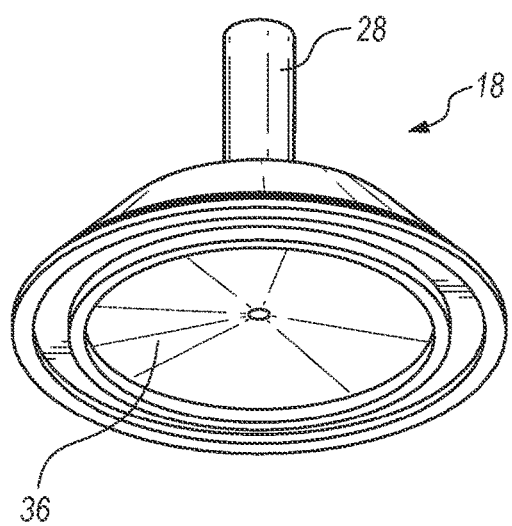
FIG. 14D is a bottom perspective view of the stethoscope chest piece of the present invention.

EXAMPLE: To test the invention, a smartphone 16 was attached to the attachment device 10. The neck 28 of a stethoscope chest piece 18 was then pushed through the port 26 of the attachment device 10. The smartphone and the stethoscope chest piece attached to the attachment device 10 is shown in FIG. 9. The stethoscope chest piece was placed over the chest of the user. The microphone of the smartphone received the sounds from the chest piece, and a voice recorded app on the smartphone was used to record the sound. The sound file was then sent to a computer and analyzed using the Audacity software program. The sound waves from the sound file is shown in FIG. 13 with heartbeats 34 noted. Each heartbeat 34 includes a first heart sound and a second heart sound. From a review of the sound waves image and the sound recording, a physician was able to analyze the condition of the user and provide a healthy assessment of the user.

In another embodiment, the app is configured to diagnose the patient without the assistance of the medical professional by utilizing an artificial intelligence algorithm. The artificial intelligence algorithm was trained by recording sounds from a SAM II® manikin. The manikin has internal speakers to simulate the sounds of the body. The sounds from the manikin were labeled by type (e.g., normal, mitral regurgitation, S3 heart sounds, arrythmias, etc.). Those sounds were then processed by filtering noise with a high pass or low pass filter and converted into arrays of numbers (matrices). Fast Fourier transforms were performed, and then mel frequencies, zero-crossings, and spectral roll off numbers were calculated. All of these metrics were inputs that trained the artificial intelligence algorithm.

Once the patient's sounds are recorded on the smart device 16 and the noise filtering is performed as discussed above, the sounds are converted to an array of numbers (i.e., a matrix). Mel frequencies, zero crossings and a fast Fourier transform are performed based on the sounds. All of these metrics are inputted to the artificial intelligence algorithm. As discussed above, the artificial intelligence algorithm is trained to identify and classify the types of sounds (e.g., abnormal, normal, artifacts). If the patient's sound is considered to be an artifact, the mobile app requests the patient to record the sound again. All of the recorded sounds are sent to the medical professional with a label with probabilities of a possible medical condition, such as normal 90%, abnormal 5%, and artifact 5%. This allows the medical professional to have a guide before listening to the sound.

Figure 10:
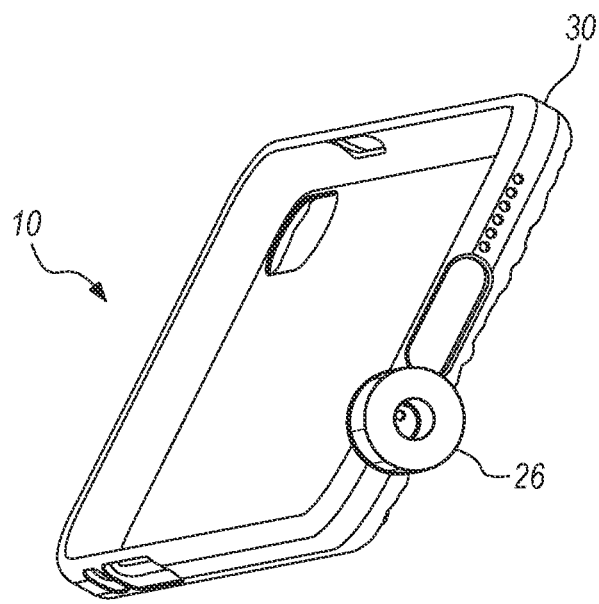
FIG. 10 is a side perspective view of a second preferred embodiment of the attachment device.
Figure 11:
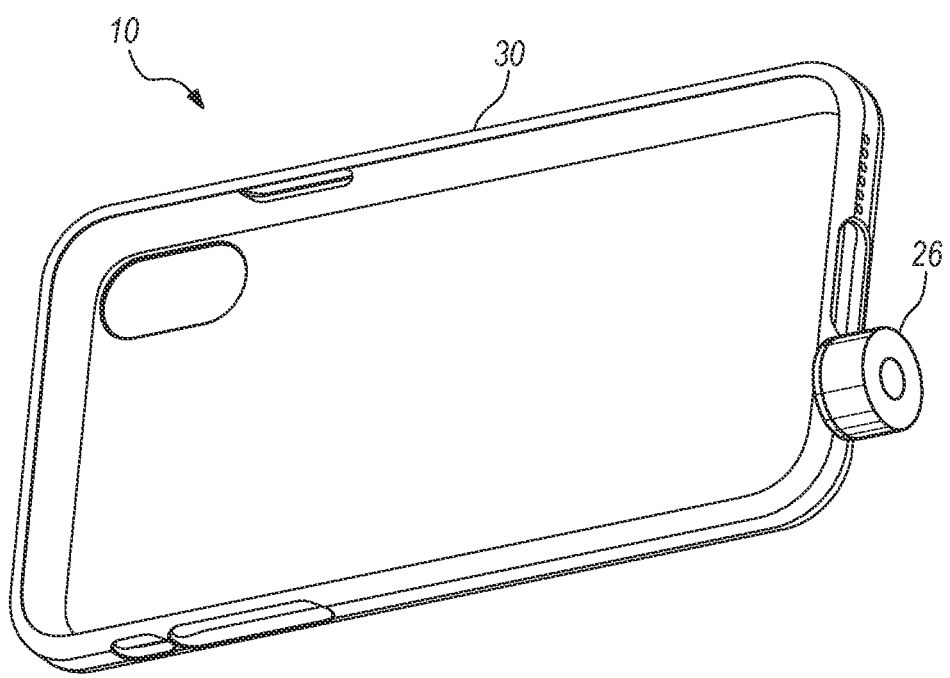
FIG. 11 is a side perspective view of a second preferred embodiment of the attachment device.
Figure 12:
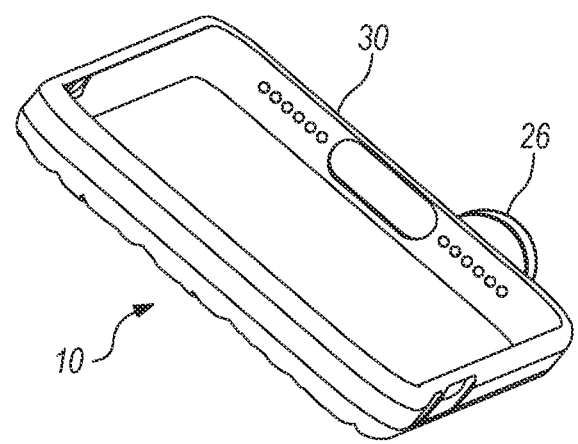
FIG. 12 is a side perspective view of a second preferred embodiment of the attachment device.

An alternative embodiment of the attachment device 10 of the present invention is shown in FIGS. 10-12. In this embodiment, the attachment device 10 includes a smart device case 30 with a port 26 for receiving the auscultation device 12. The port 26 preferably includes a cylindrical channel that extends from the base of the smart device case 30. The port 26 preferably is positioned such that the microphone of the smart device 16 will be positioned directly over the port 26 when the smart device 16 is positioned inside the smart device case 30. The neck 28 of the stethoscope chest piece 18 is inserted into the port 26 by sliding the neck into the port and pushing the neck until the end of the neck is touching the surroundings of the microphone 14 of the smart device 16 in the smart device case 30.

The present invention has been described with reference to certain preferred and alternative embodiments that are intended to be exemplary only and not limiting to the full scope of the present invention.

We claim:

1. An attachment device for holding an auscultation device near a smart device, said attachment device comprising:
    a first arm and a second arm, wherein said first arm and said second arm are joined to a connection portion, wherein said connection portion comprises an interior compartment, wherein said attachment device has an open position and a closed position; and
    a port extending from the interior compartment of said connection portion to an exterior of said connection portion,
    wherein said interior compartment of said connection portion is operable to receive a smart device when said attachment device is in said open position and said port is operable to receive an auscultation device, wherein said attachment device is configured such that a microphone of said smart device is positioned adjacent to said auscultation device when said connection portion receives said smart device and said port receives said auscultation device,
    wherein said first arm comprises a free end and a connected end and said second arm comprises a free end and a connected end, wherein said connected end of said first arm is joined to said connection portion and said connected end of said second arm is joined to said connection portion, wherein said free end of said first arm and said free end of said second arm are operable to contact said auscultation device when said smart device is received in said interior compartment.

2. The attachment device of claim 1, wherein said interior compartment comprises a plurality of cushions.

3. The attachment device of claim 1, wherein said port is positioned in a bottom of said interior compartment.

4. The attachment device of claim 1, wherein a support is positioned adjacent said port.

5. The attachment device of claim 1, wherein said auscultation device is a stethoscope chest piece comprising a neck, and wherein said stethoscope chest piece comprises a bell or a diaphragm.

6. The attachment device of claim 5, wherein said port is operable to receive said neck.

7. The attachment device of claim 6, wherein said neck extends perpendicularly to a face of said bell.

\* \* \* \* \*